US00PP34137P2

(12) United States Plant Patent
Brinkmann

(10) Patent No.: US PP34,137 P2
(45) Date of Patent: Apr. 19, 2022

(54) RASPBERRY PLANT NAMED 'PLAPINK 14103'

(50) Latin Name: ***Rubus idaeus* L.**
Varietal Denomination: Plapink 14103

(71) Applicant: Plantas de Navarra, S.A. Sociedad Unipersonal, Valtierra (ES)

(72) Inventor: Michael Brinkmann, Navarra (ES)

(73) Assignee: Plantas de Navarra, S.A. Sociedad Unipersonal, Navarra (ES)

( * ) Notice: Subject to any disclaimer, the term of this patent is extended or adjusted under 35 U.S.C. 154(b) by 0 days.

(21) Appl. No.: 17/381,620

(22) Filed: Jul. 21, 2021

(30) Foreign Application Priority Data

Oct. 6, 2020 (QZ) ..... PBR 2020/2451
Dec. 28, 2020 (MA) ..... 1037/20
Jan. 6, 2021 (MX) ..... 3341

(51) Int. Cl.
*A01H 5/08* (2018.01)
*A01H 6/74* (2018.01)

(52) U.S. Cl.
USPC ..... Plt./204

(58) Field of Classification Search
USPC ..... Plt./203, 204
See application file for complete search history.

*Primary Examiner* — Susan McCormick Ewoldt
(74) *Attorney, Agent, or Firm* — Knobbe, Martens, Olson & Bear, LLP

(57) ABSTRACT

The new raspberry variety 'Plapink 14103' is characterized by a combination of traits which include, but are not limited to, medium vigor plants having an arching growth habit, and producing broad, conical-shaped and light-red colored fruit.

18 Drawing Sheets

Botanical classification: *Rubus idaeus* L.
Variety denomination: 'Plapink 14103'.

CROSS-REFERENCE TO RELATED APPLICATIONS

This application claims the benefit of European Community Plant Variety Office Application No. 2020/2451, filed on Oct. 6, 2020, Moroccan Plant Variety Application No. 1037/20, filed Dec. 28, 2020, and Mexican Plant Variety Application No. 3341, filed Jan. 6, 2021, each of which is incorporated by reference herein in its entirety.

BACKGROUND

Disclosed herein is a new and distinct raspberry variety. The varietal denomination of the new variety is 'Plapink 14103'. The new variety was designated by the breeder as breeder number '14.17R.05'. The new variety of raspberry was created in a breeding program by crossing two parents. The seed parent was an undistributed raspberry variety designated '06.13R.46' (unpatented) and the pollen parent was an undistributed raspberry variety designated '08.10R.12' (unpatented). Each parent was a selection from a breeder's program and has not been commercialized.

The resulting seedling of the new variety was grown and asexually propagated by Michael Brinkmann by root cuttings in Segovia, Spain, 3°59'W., 41°22'N., at 2742 feet elevation. Clones of the new variety were further asexually propagated and extensively tested. This propagation and testing has demonstrated that the combination of traits disclosed herein which characterize the new variety are fixed and retained true to type through successive generations of asexual reproduction.

The new variety 'Plapink 14103' is characterized by a vigorous plant with consistent fruit production from the end of September through the end of December on primocanes and in the ensuing year beginning in April and again beginning in June. In addition, the new variety has an arching plant habit and very abundant production of light-red colored (RHS red group color near 41 B to 41 A), broad, conical-shaped, medium-sized fruit having strong glossiness.

COMPARISON TO THE PARENT VARIETIES

The new variety is distinguishable from the parental varieties by the following characteristics possessed by 'Plapink 14103' which are different than, or not possessed, by the seed parent designated '06.13R.46' (unpatented) and/or the pollen parent designated '08.10R.12' (unpatented).

The stipules in the leaf of the seed parent '06.13R.46' (unpatented) are longer than in the leaf of the new variety 'Plapink 14103'.

Overlapping of lateral leaflets with the terminal leaflet is absent in the leaf of the seed parent '06.13R.46' (unpatented), whereas in the leaf of the new variety 'Plapink 14103' overlapping is present.

The leaf of the seed parent '06.13R.46' (unpatented) has a dark green color (RHS green group color near 131 C to 131 B) on the upper side, whereas the leaf of the new variety 'Plapink 14103' has a medium green (RHS green group color near 137 C to 137 B) color on the upper side.

The pollen parent '08.10R.12' (unpatented) shows an upright habit, whereas the new variety 'Plapink 14103' shows an arching habit.

The fruit of the pollen parent '08.10R.12' (unpatented) is bigger than fruit of the new variety 'Plapink 14103'.

The shape of the fruit of the pollen parent '08.10R.12' is conical and has a plug that is longer than it is broad, whereas the new variety 'Plapink 14103' has fruit with a broad conical shape and a plug that is moderately longer than it is broad.

COMPARISON TO CLOSEST VARIETY

The new variety 'Plapink 14103' is believed to be closest to the variety 'Adelita' (U.S. Plant Pat. No. 25,245), but is distinguished therefrom by the following characteristics possessed by 'Plapink 14103' which are different than, or not possessed by 'Adelita' (U.S. Plant Pat. No. 25,245).

The plant habit of Adelita' (U.S. Plant Pat. No. 25,245) is upright, whereas 'Plapink 14103' shows an arching plant habit. The difference in the plant habit of 'Plapink 14103' (designated '14.17R.05') and 'Adelita' (U.S. Plant Pat. No. 25,245) is shown in FIG. 17 and FIG. 18.

The current season's cane of 'Adelita' (U.S. Plant Pat. No. 25,245) shows a medium to strong anthocyanin coloration, whereas in the current season's cane of 'Plapink 14103' anthocyanin coloration is absent or very weak. 'Adelita' (U.S. Plant Pat. No. 25,245) also shows a sparse density of spines, whereas 'Plapink 14103' shows a medium density of spines. Differences in the anthocyanin coloration of the current season's cane and spine density of 'Plapink 14103' (designated '14.17R.05') and 'Adelita' (U.S. Plant Pat. No. 25,245) are shown in FIG. 7 and FIG. 8.

The length/width ratio of the fruit of 'Adelita' (U.S. Plant Pat. No. 25,245) is large, whereas the length/width ratio of the fruit of 'Plapink 14103' small to medium. Differences in fruit size, length/width ratio, fruit shape and fruit color of 'Plapink 14103' (designated '14.17R.05') and 'Adelita' (U.S. Plant Pat. No. 25,245) are shown in FIG. 15.

The fruit of 'Adelita' (U.S. Plant Pat. No. 25,245) shows a conical shape and red color (RHS red group near 47 A to 46 A), whereas the fruit of 'Plapink 14103 shows a broad conical shape and a light red color (RHS red group color near 41 B to 41 A).

The plug size of the fruit of 'Adelita' (U.S. Plant Pat. No. 25,245) is bigger than the plug size of fruit of 'Plared 14103'. The difference in the plug size of 'Plapink 14103' (designated '14.17R.05') and 'Adelita' (U.S. Plant Pat. No. 25,245) is shown in FIG. 16.

The fruit of 'Adelita' (U.S. Plant Pat. No. 25,245) shows medium to strong adherence to the plug, whereas the fruit of 'Plapink 14103' shows a weak adherence to the plug.

The time of the beginning of flowering on current season's cane of 'Adelita' (U.S. Plant Pat. No. 25,245) is early to medium, whereas the time of the beginning of flowering on currents season's cane of 'Plapink 14103' is medium to late.

The time of beginning of fruit ripening on current year's cane of 'Adelita' (U.S. Plant Pat. No. 25,245) is early, whereas the time of beginning of fruit ripening on current year's cane of 'Plapink 14103' is medium.

These differences are maintained during the harvest season.

BRIEF DESCRIPTION OF THE ILUSTRATIONS

The accompanying photographs show typical specimens of the new variety 'PLAPINK 14103' including fruit, foliage and flower, in color as nearly true as is reasonably possible in color illustrations of this character.

The plants depicted in the drawings were planted Jun. 10, 2019 in the farm of La Mogalla in Cartaya (Huelva), Spain, about 7°W, 37°N, 45 feet elevation. Photographs were taken in about Nov. 4 and Nov. 12, 2019 when there was a minimum temperature of about 7 to 9° C. and a maximum temperature about 18 to 22° C.

FIG. 1 and FIG. 2 show several plants of the new variety (designated '14.17R.05') which exhibit an arching plant habit with several light red-colored and broad conical-shaped fruit.

FIG. 3 and FIG. 4 show the upper side and the underside, respectively, of a complete leaf of the new variety (designated '14.17R.05'). It can be seen that the upper side of the leaf of the new variety (designated '14.17R.05') is medium green (RHS green group near 137 C to 137 B) and the underside of the leaf is dark green color (RHS green group near 138 C to 138 B). It can be seen in the photographs that the lateral leaflets in the leaf of the new variety (designated '14.17R.05') are touching.

FIG. 5 and FIG. 6 show the upper side and the underside, respectively, of a terminal leaflet of the new variety (designated '14.17R.05'). In it we can see that the terminal leaflet color of upper side of the new variety '(designated '14.17R.05') is a medium green (RHS green group near 137 C to 137 B) and the terminal leaflet color of underside of the new variety (designated '14.17R.05') is a dark green (RHS green group near 138 C to 138 B).

FIG. 7 shows the current season's cane of the new variety (designated '14.17R.05') with an absent or very weak anthocyanin coloration and a medium spine density.

FIG. 8 shows the current season's cane of 'Adelita' (U.S. Plant Pat. No. 25,245) with a greyed-purple anthocyanin coloration (RHS greyed-purple group near 183 D to 183 C) and a sparse spine density.

Figure 1:
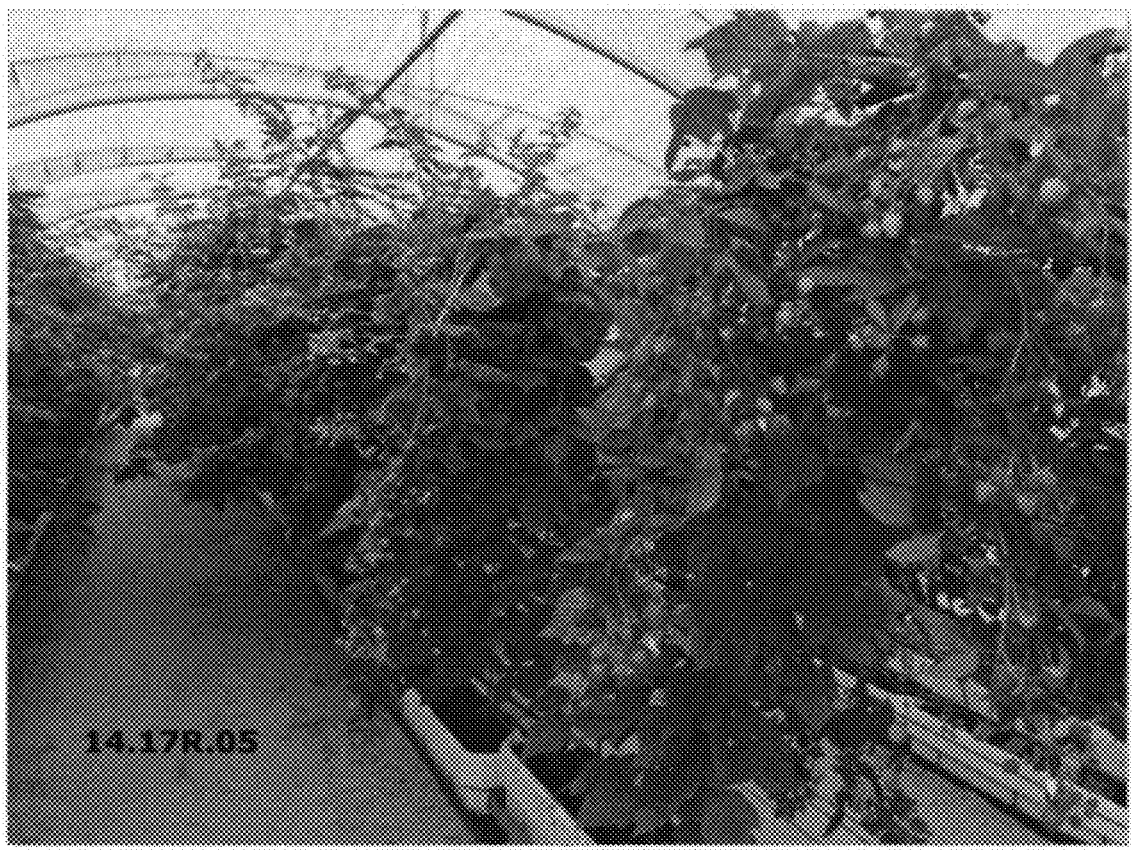
Figure 2:
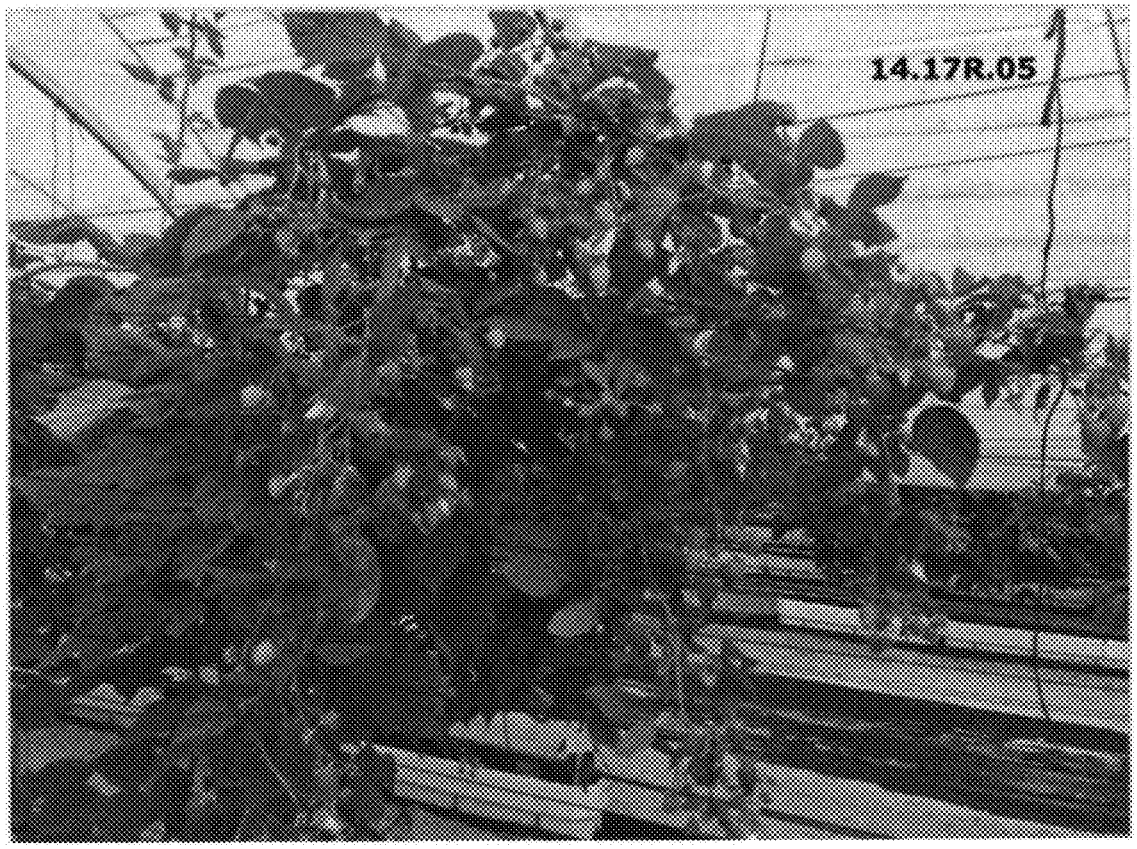
Figure 3:
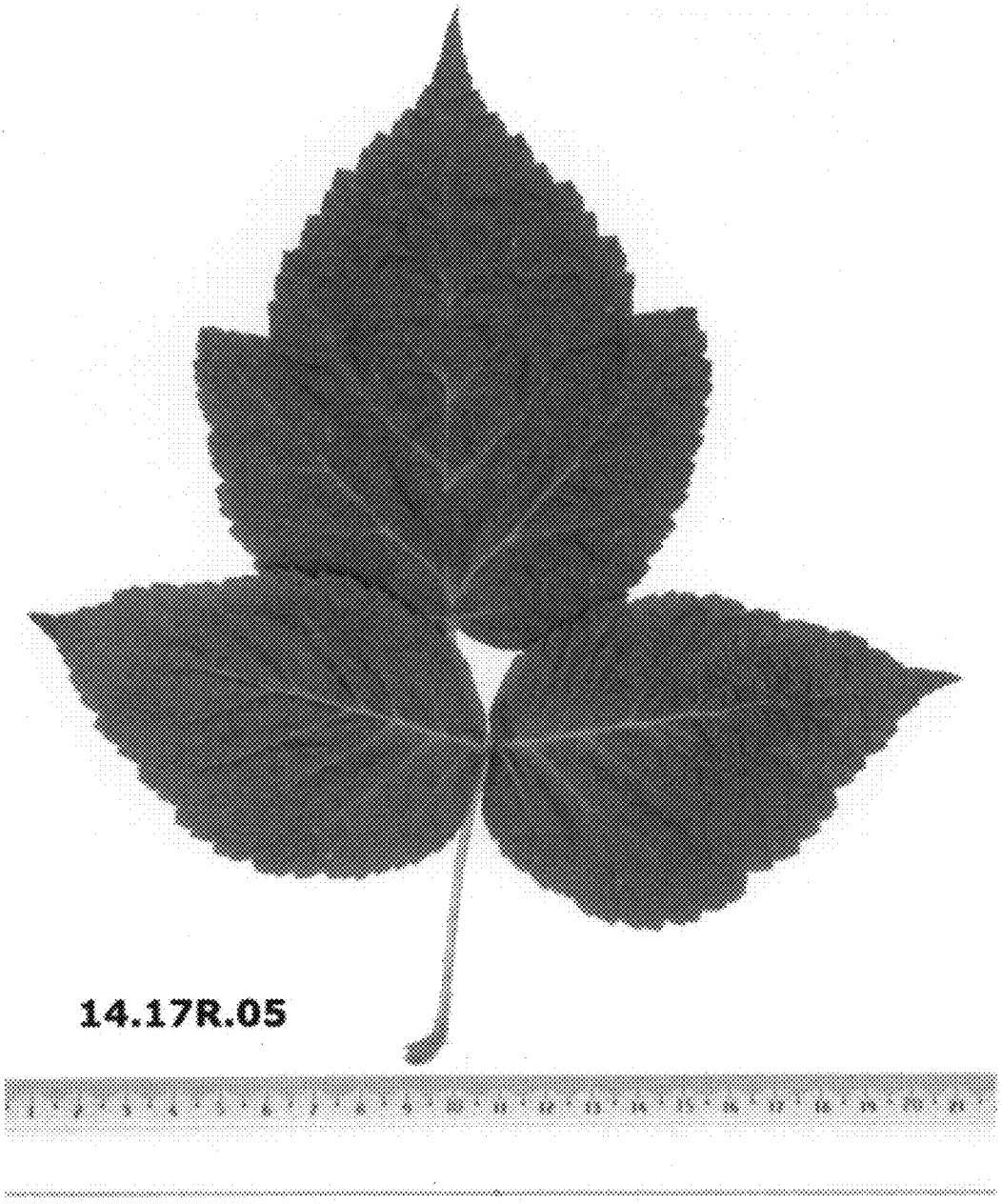
Figure 4:
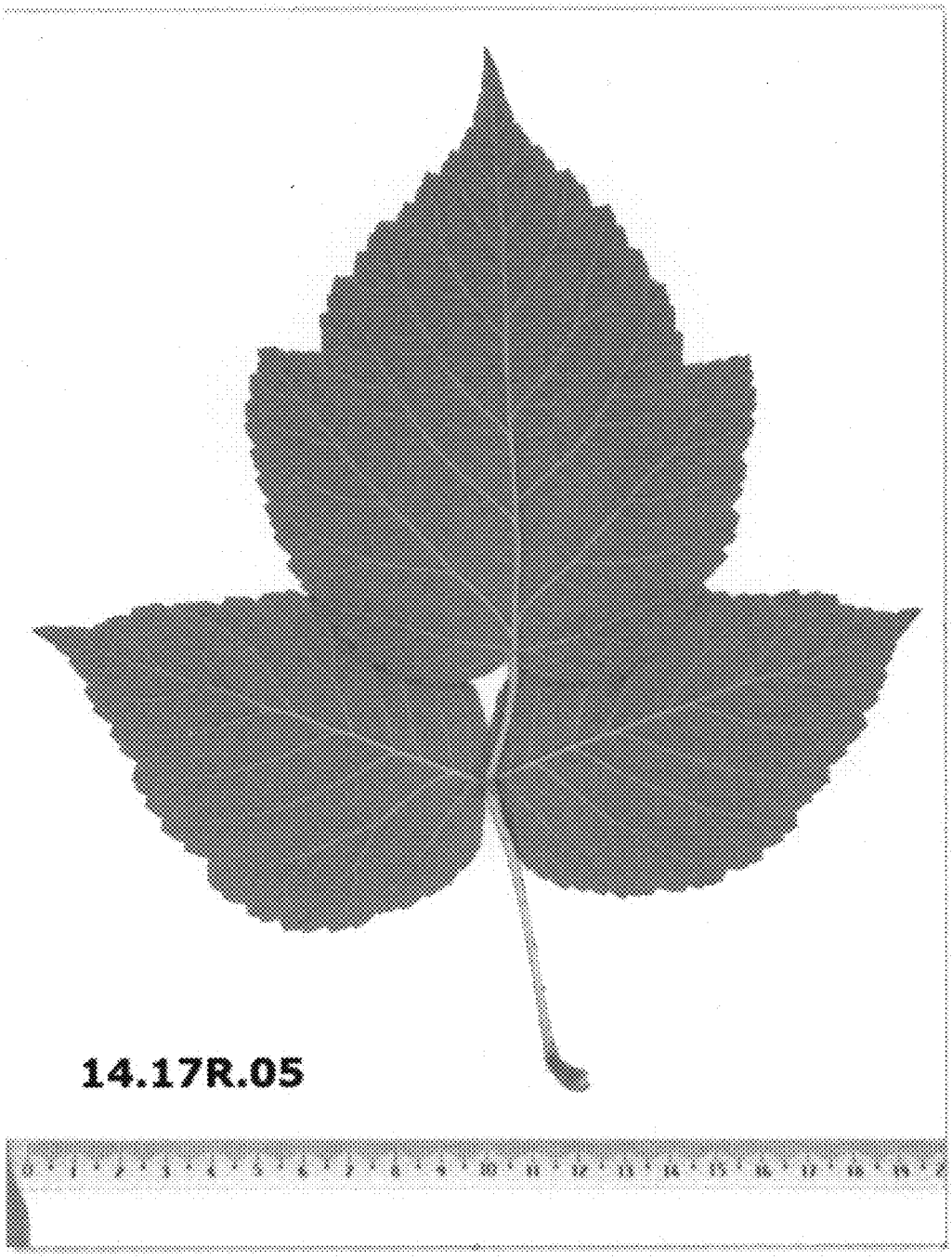
Figure 5:
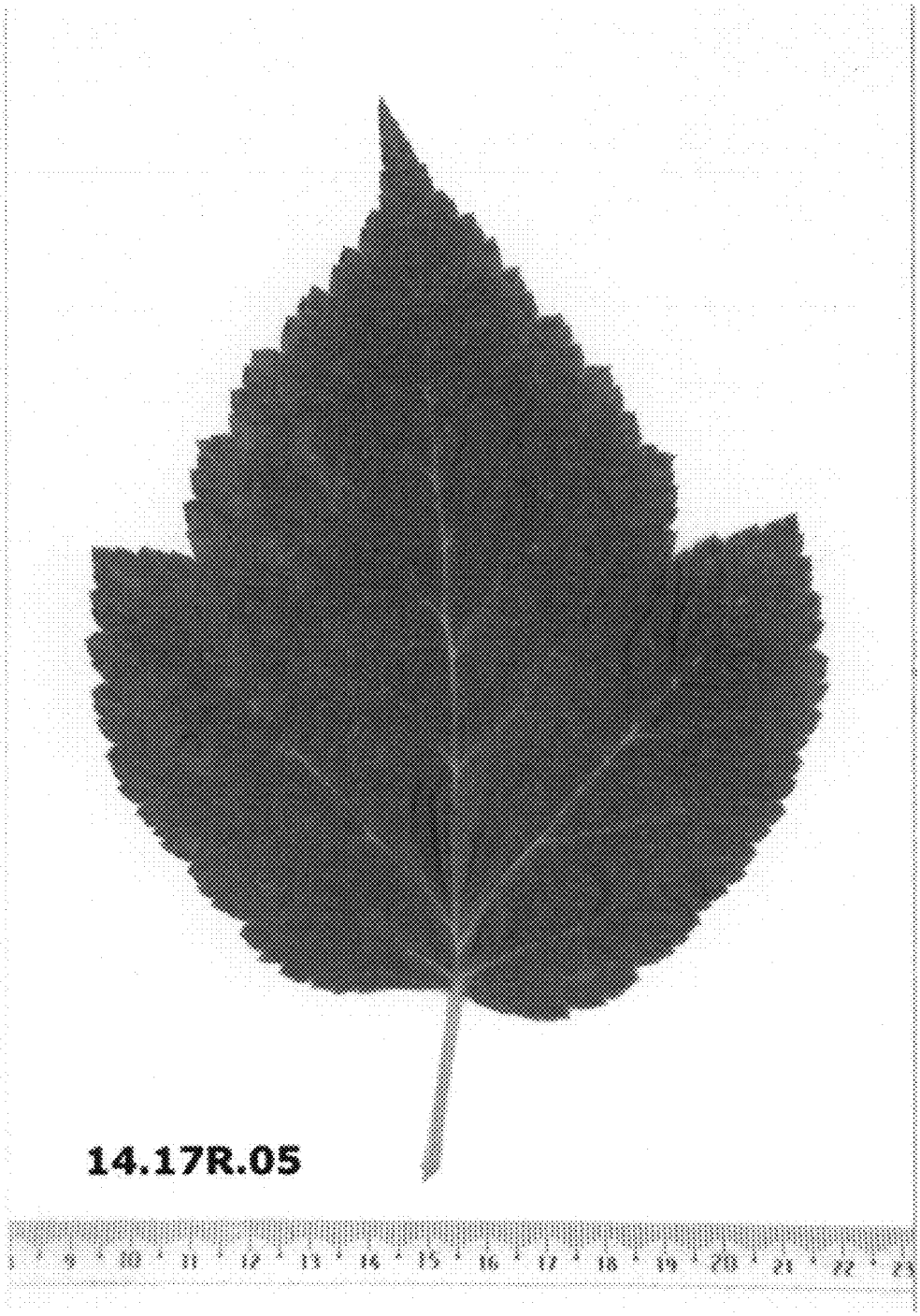
Figure 6:
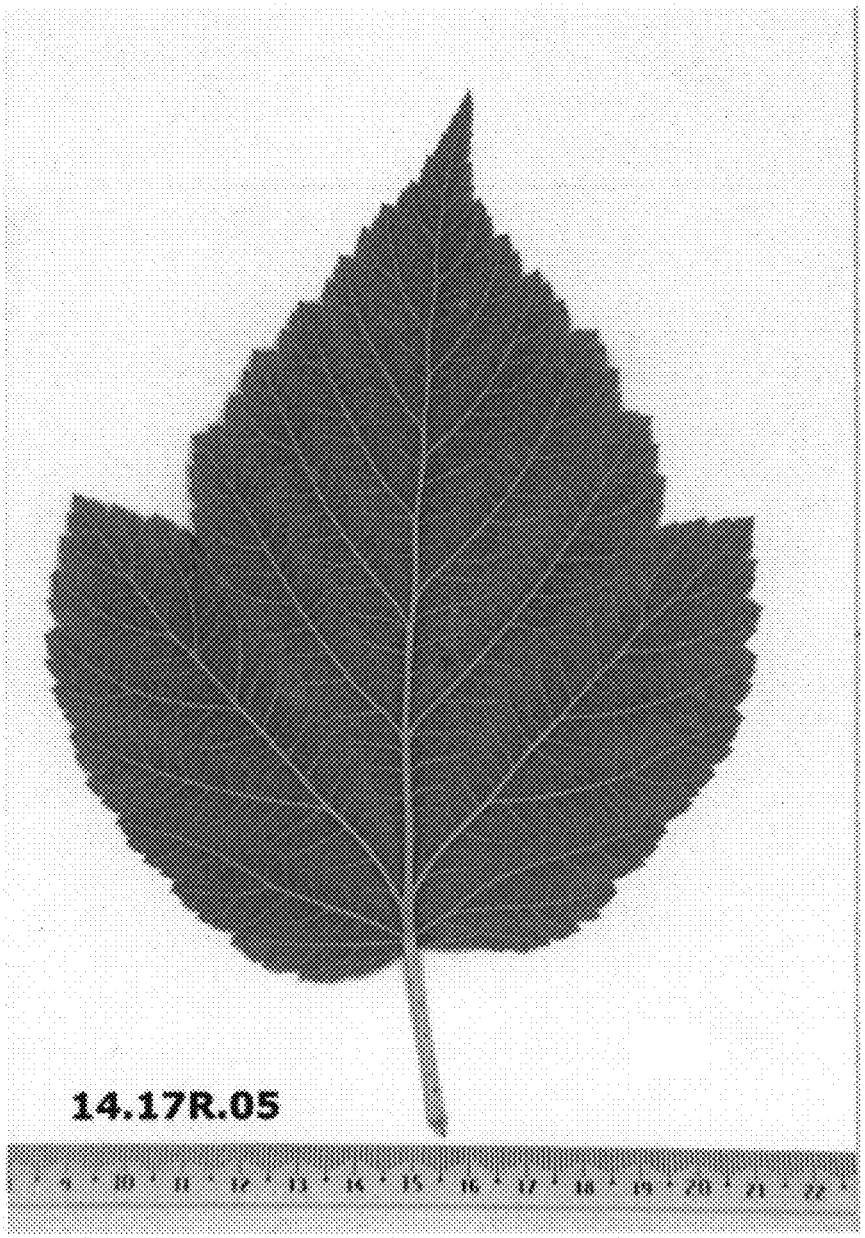
Figure 7:
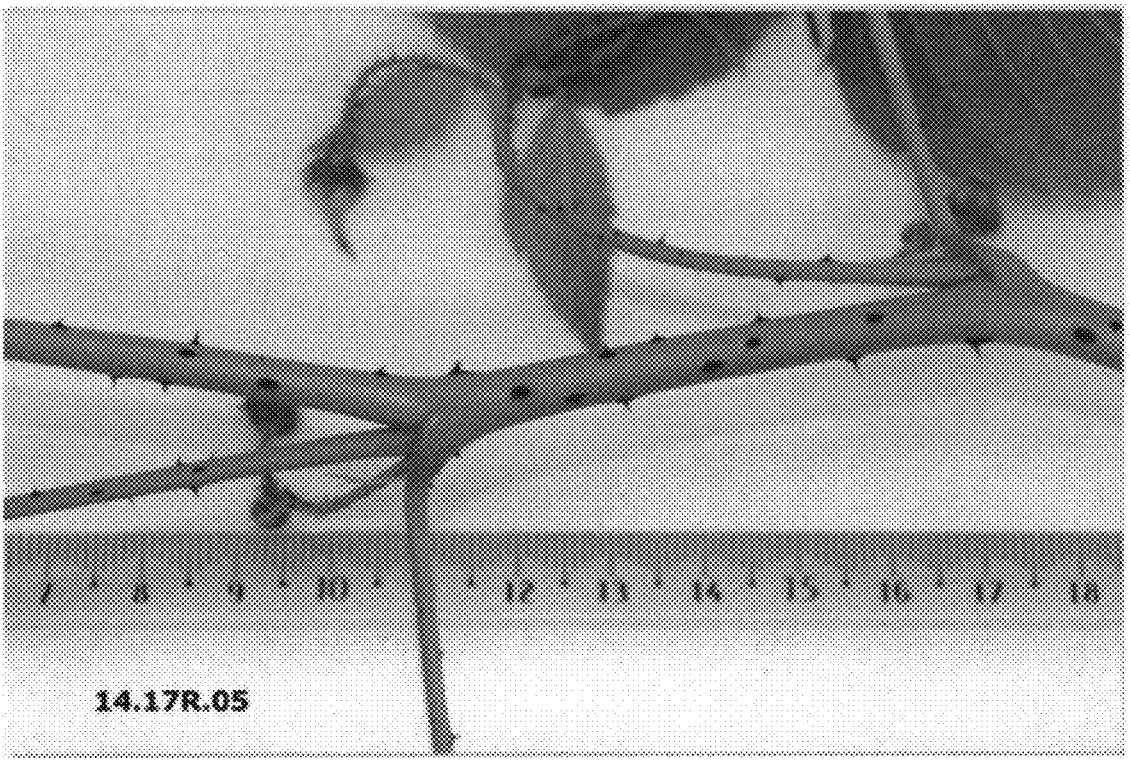
Figure 8:
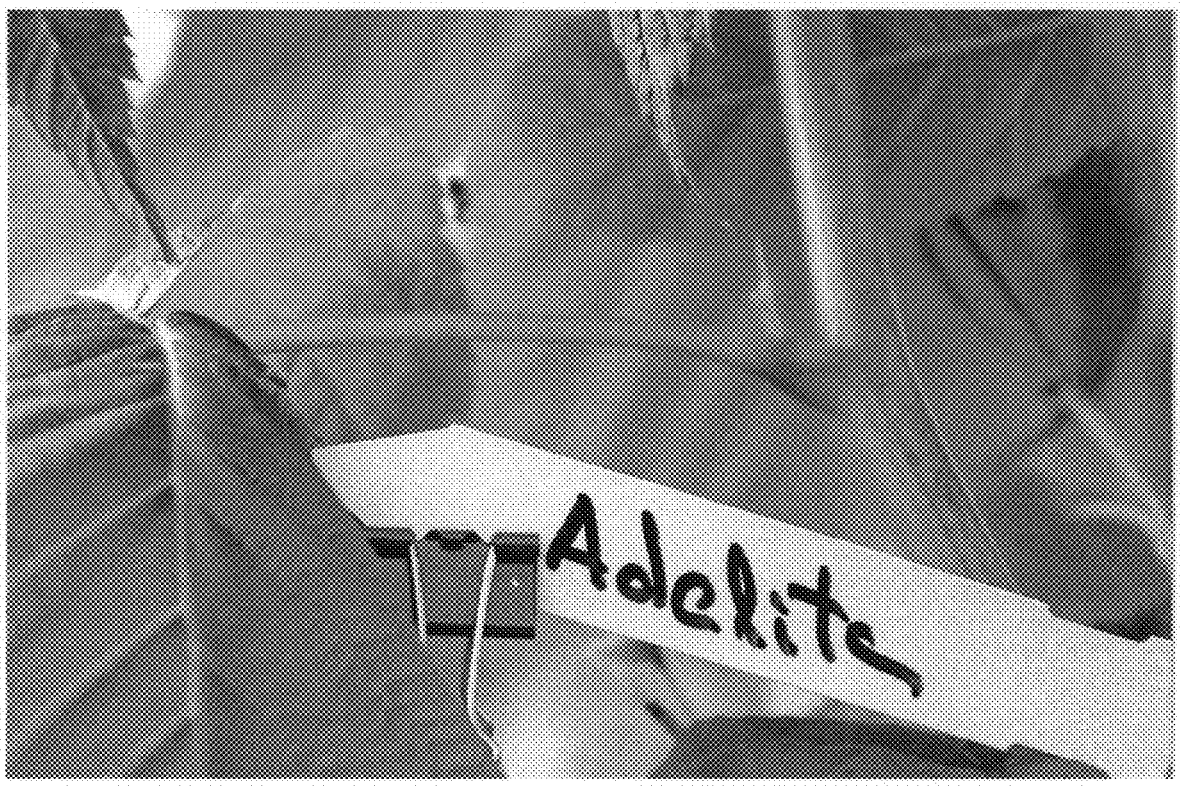
Figure 9:
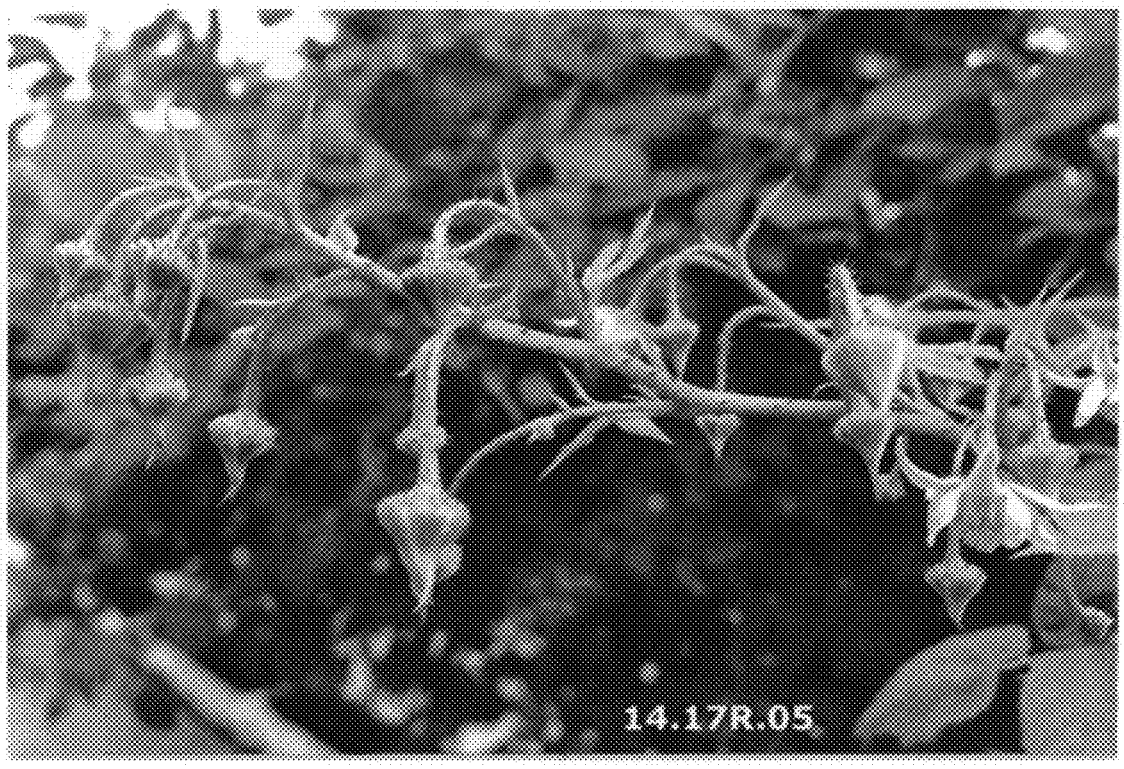
FIG. 9 shows typical flower buds of the new variety (designated '14.17R.05') with trapezoidal shape and green color (RHS green group near 138 D to 138 C).
Figure 10:
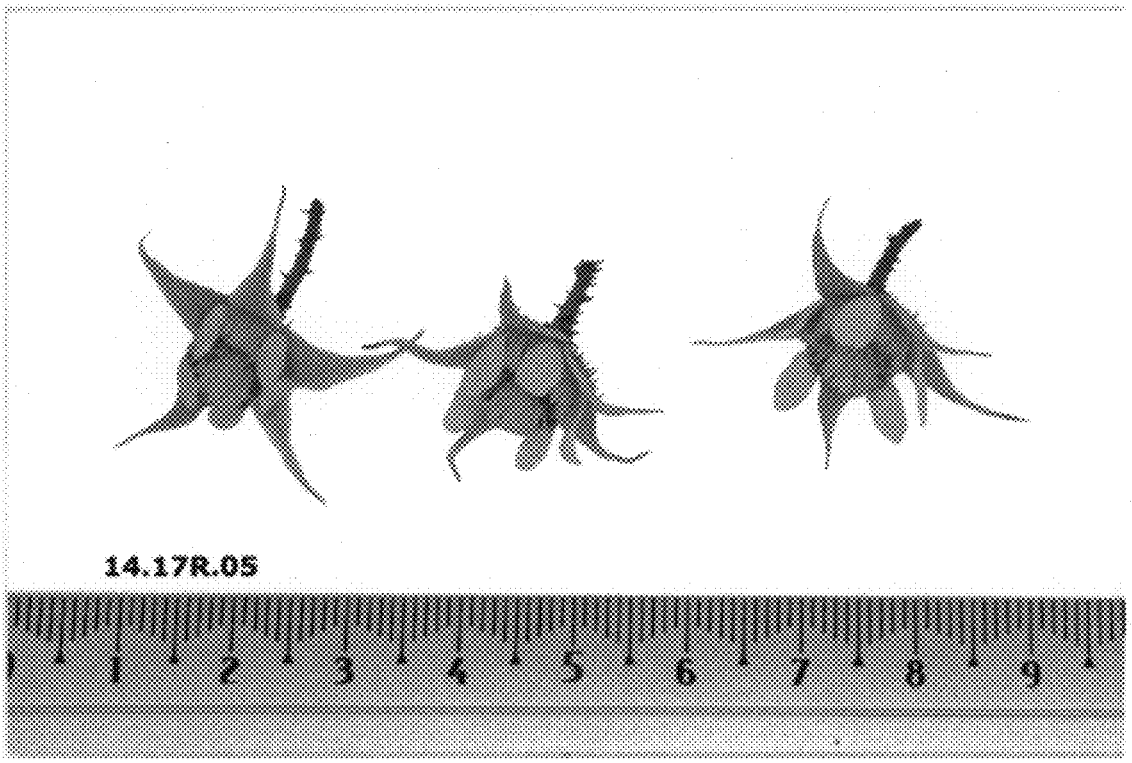
FIG. 10 shows typical flowers of the new variety (designated '14.17R.05').
Figure 11:
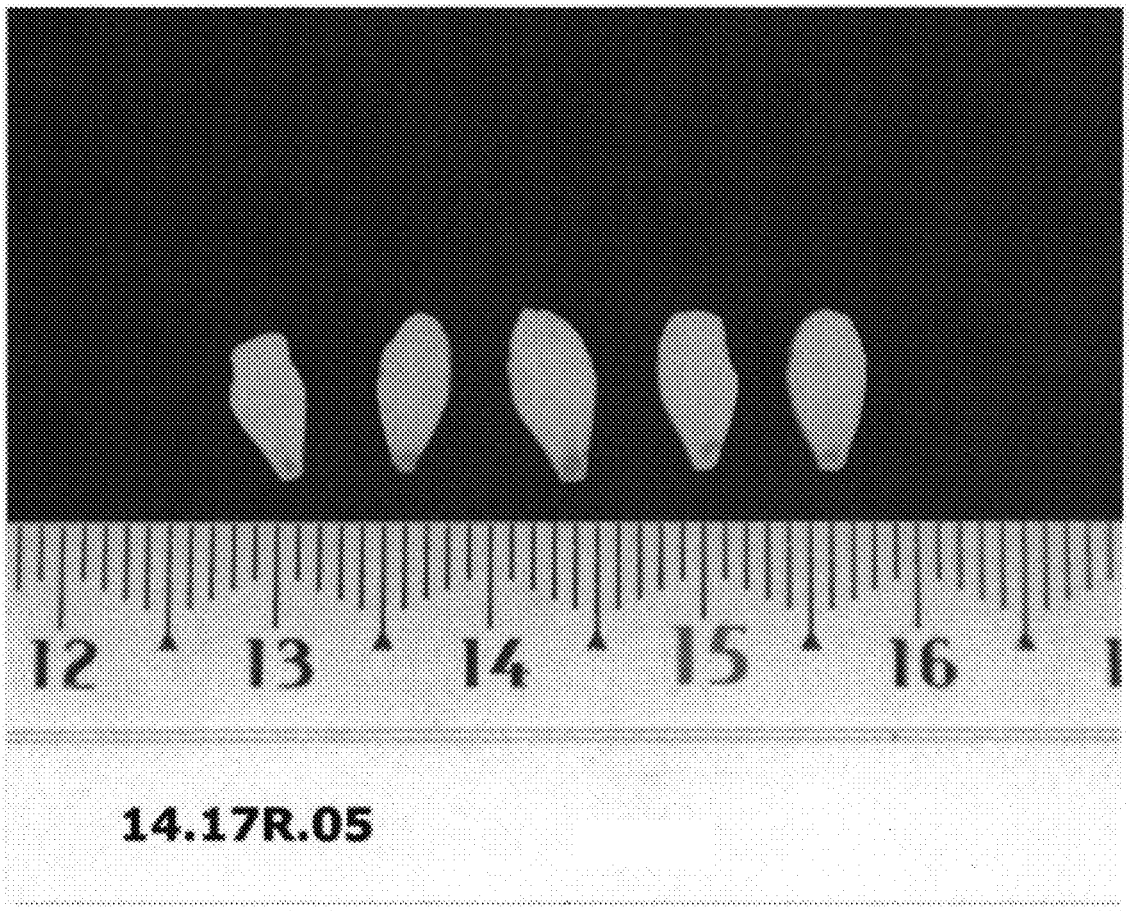
FIG. 11 shows typical petals of the new variety (designated '14.17R.05') with a narrow elliptical shape and white color (RHS white group near 155 C).
Figure 12:
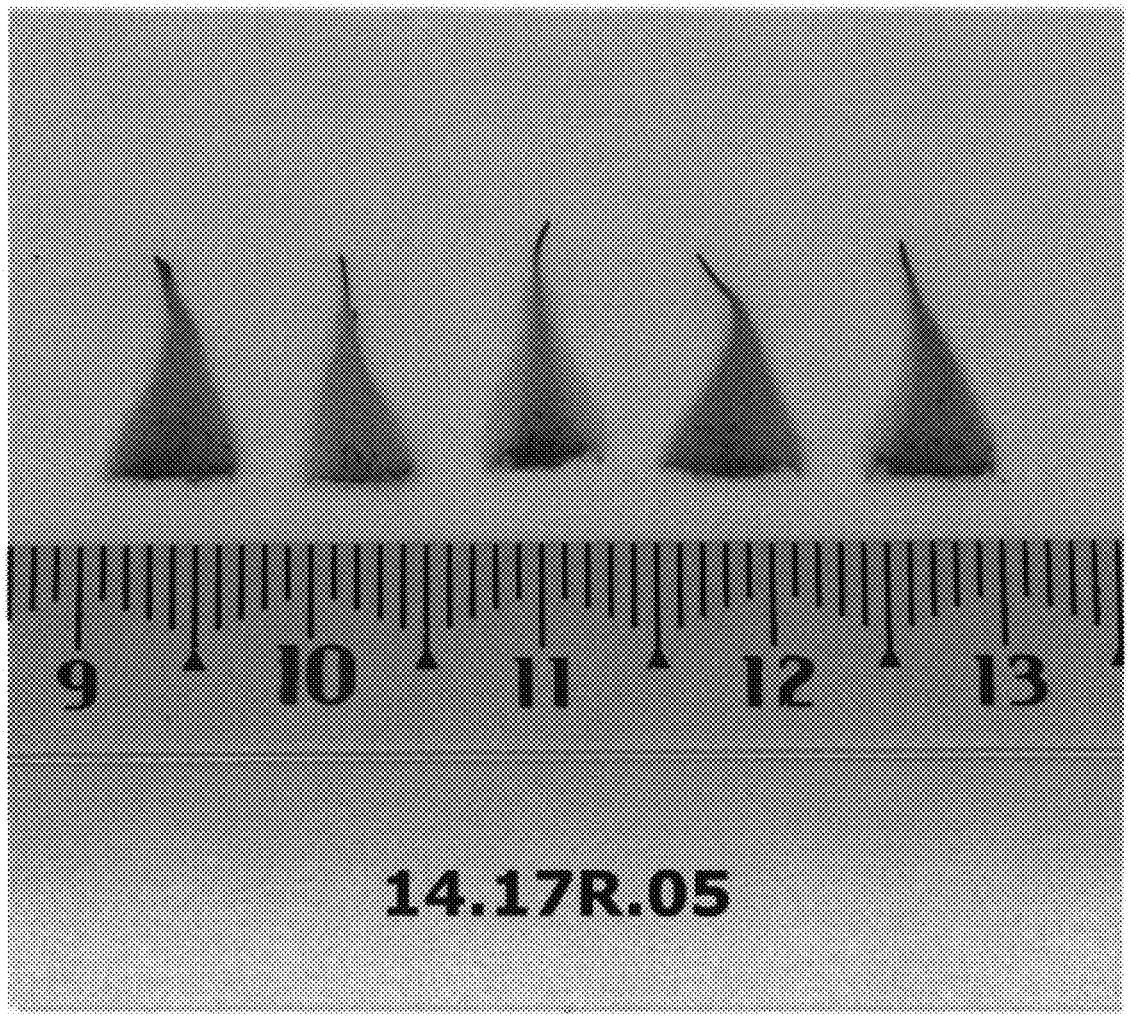
FIG. 12 shows typical sepals of the new variety (designated '14.17R.05') with triangular shape, acuminate apex and green color (RHS green group near 145 C to 145 B).
Figure 13:
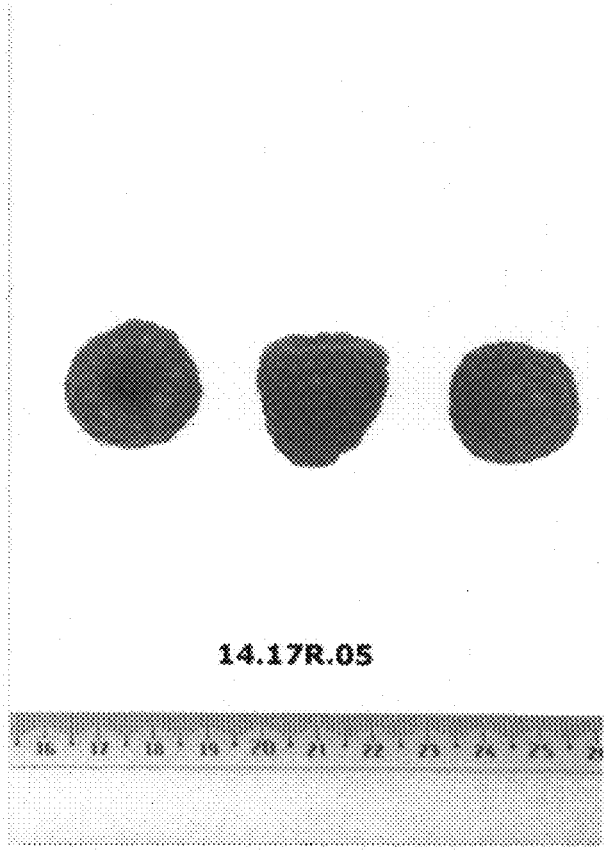
FIG. 13 and FIG. 14 show typical fruits of the new variety (designated '14.17R.05') in lateral view, with a broad conical shape and red color (RHS red group near 41 B to 41 A).
Figure 14:
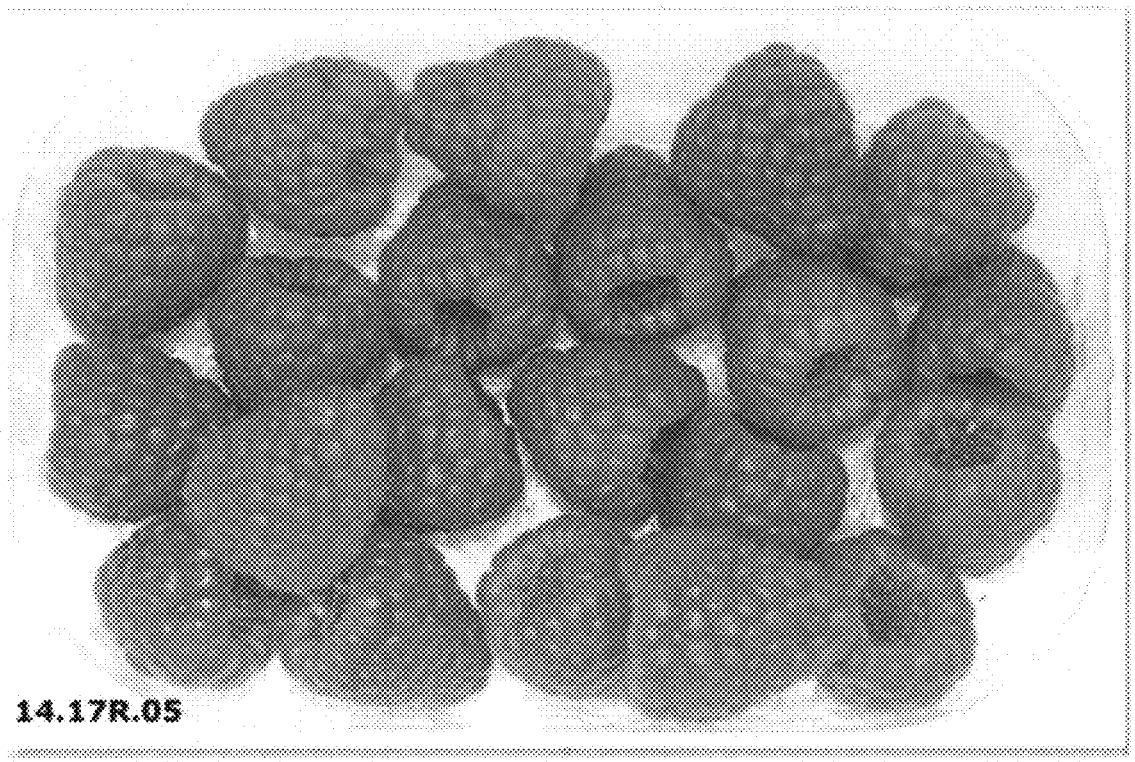
Figure 15:
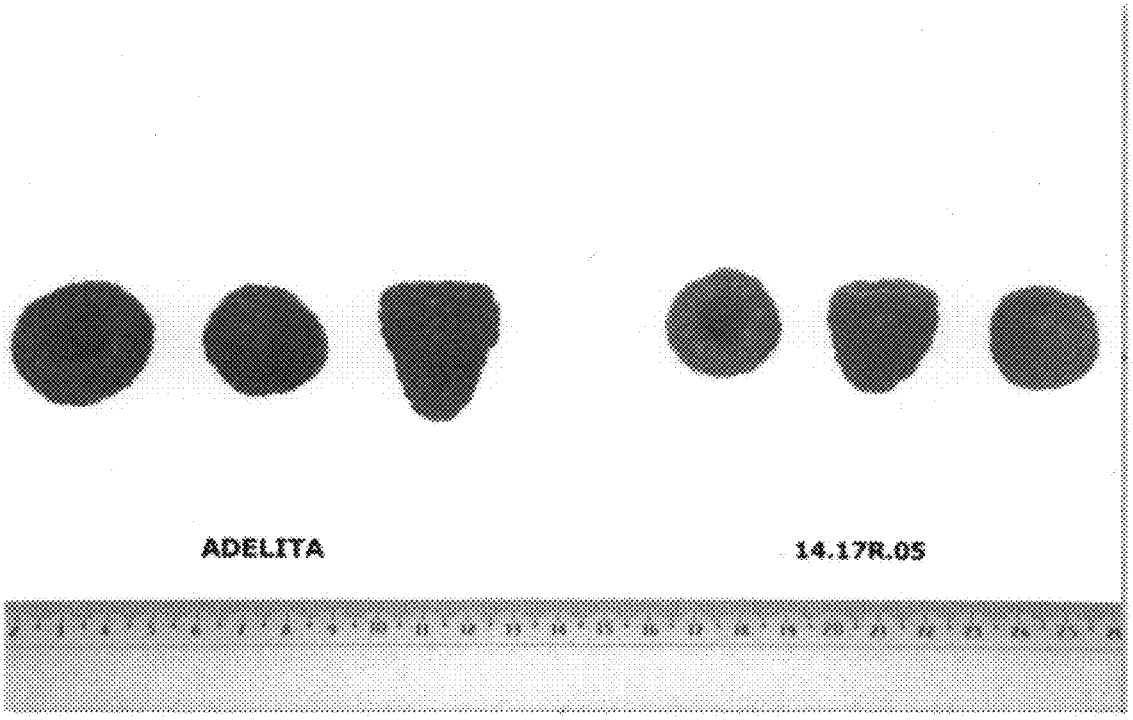

FIG. 15 shows several fruit of the new variety (designated '14.17R.05'), having a broad conical shape, a light red color (RHS red group near 41 B to 41 A), and a small to medium length/width ratio, in comparison with several fruits of 'Adelita' (U.S. Plant Pat. No. 25,245) which have a conical shape, a red color fruit (RHS red group near 47 A to 46 A) and a large length/width ratio. The fruit of 'Adelita' (U.S. Plant Pat. No. 25,245) is larger than the fruit of the new variety (designated '14.17R.05').

Figure 16:
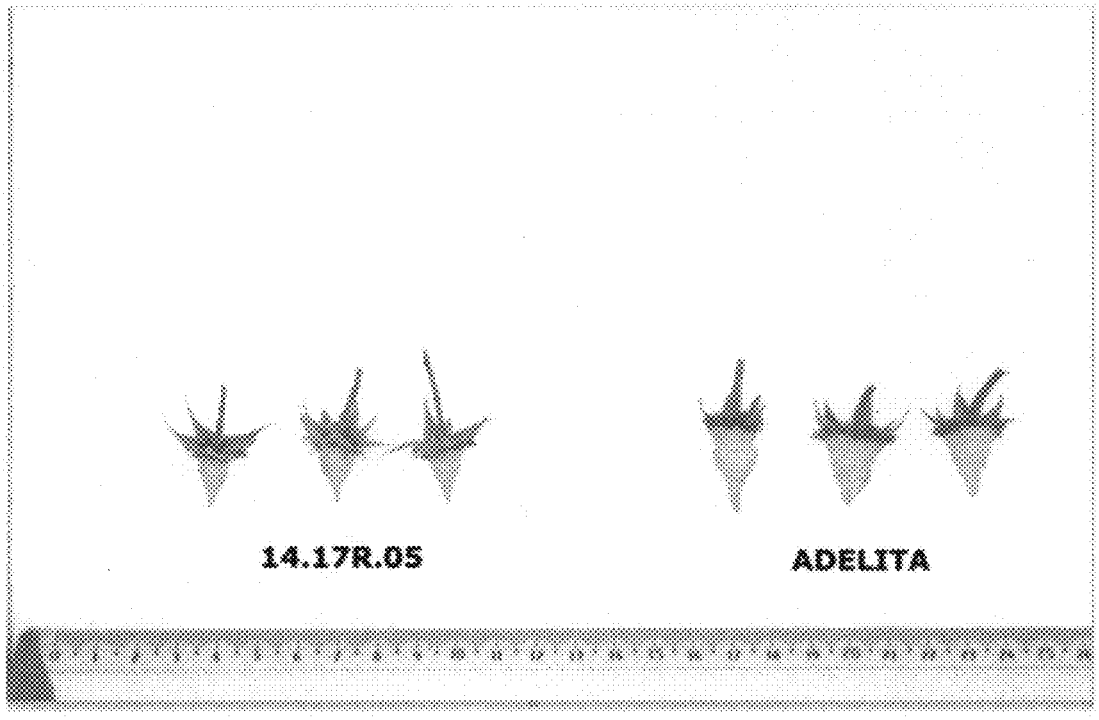

FIG. 16 shows the typical receptacle of the fruit of the new variety (designated '14.17R.05') in comparison with the receptacle of the fruit of 'Adelita' (U.S. Plant Pat. No. 25,245). The receptacle the of fruit of the new variety (designated '14.17R.05') is smaller than the receptacle of the fruit of 'Adelita' (U.S. Plant Pat. No. 25,245).

Figure 17:
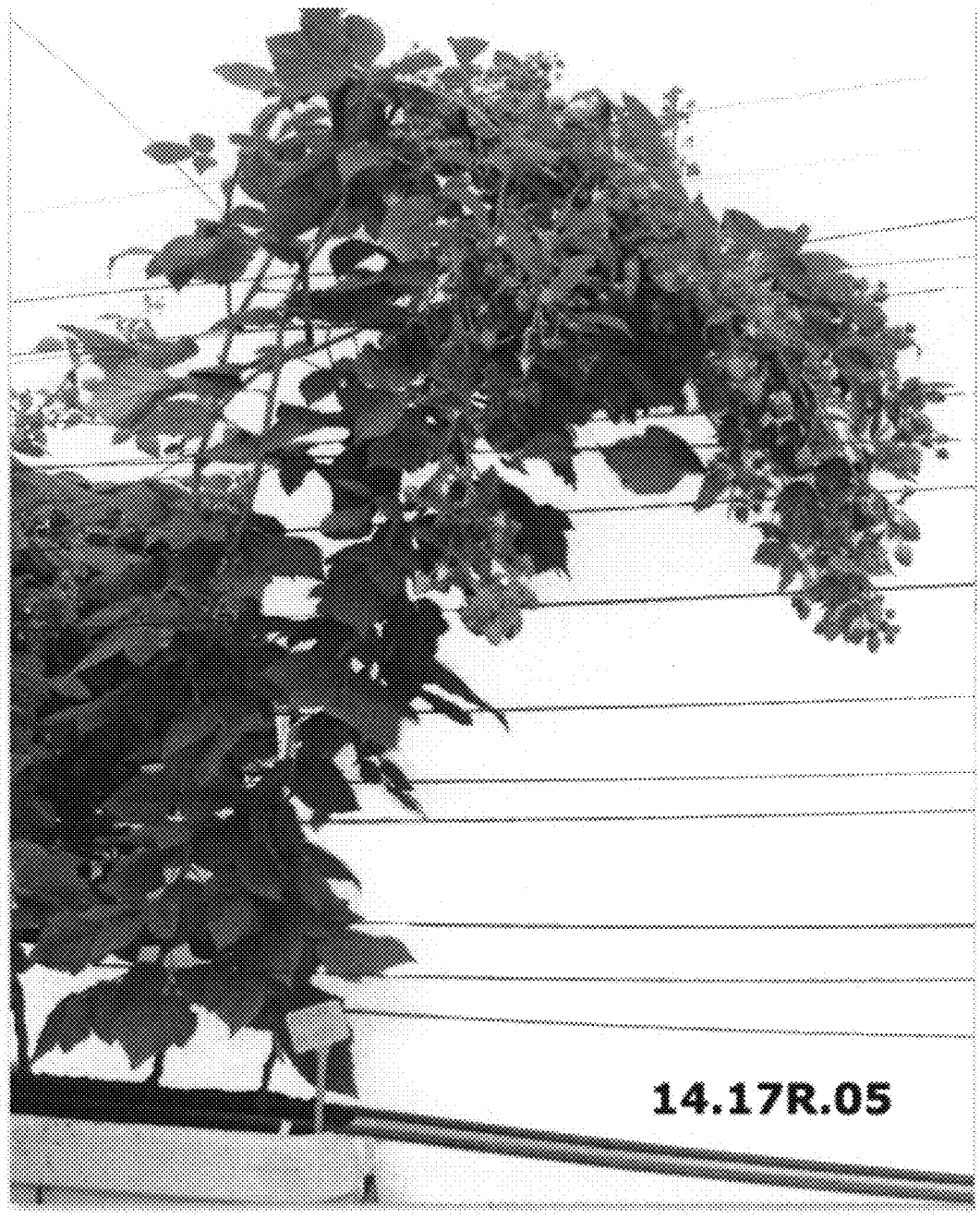

FIG. 17 shows the arching plant habit of the new variety (designated '14.17R.05').

Figure 18:
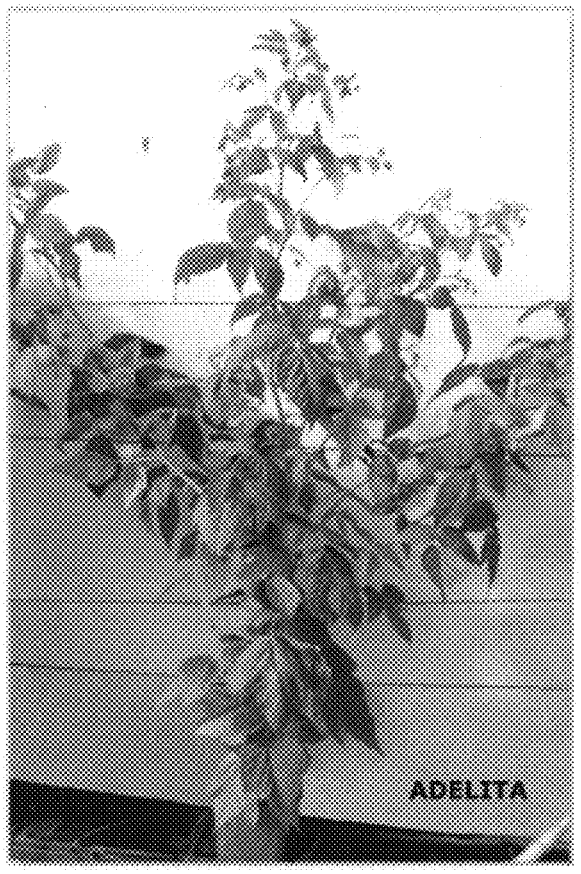

FIG. 18 shows the upright plant habit of 'Adelita' (U.S. Plant Pat. No. 25,245).

DESCRIPTION OF THE NEW VARIETY

The following detailed description of the new variety is based upon observations taken of plants and fruit grown in containers under tunnel at the farm La Mogalla in Cartaya (Huelva), Spain, 7°W., 37°N., 45 feet elevation. Water and fertilizer were applied through drip irrigation. The primocane production observations were made in Huelva (Spain) between Jun. 10, 2019 and Jun. 10, 2020. 'Plapink 14103' is a primocane variety, with consistent fruit production from the end of September through the end of December on primocanes and in the ensuing year beginning in April and beginning in June.

The following description is in accordance with UPOV terminology and the color terminology herein is in accordance with The Royal Horticultural Society Colour Chart (R.H.S.C.C.), 3$^{rd}$ edition published in 1995. The color descriptions and other phenotypical descriptions may deviate from the stated values and descriptions depending, for example, upon variation in environmental, seasonal, climatic, and cultural conditions.

PROPAGATION

The new variety is principally propagated by way of root cuttings. Although propagation by root cuttings is presently preferred, other know methods of propagating raspberry plants may be used. Raspberries root and develop well after transplanting.

'Plapink 14103' is a primocane variety with fruit production from the end of September through the end of December on primocanes and in the ensuing year beginning in April and beginning in June. It is a self-fertile variety. It produces a large quantity of pollen throughout the seasons and pollination is good.

Trials were pursued in in Cartaya (Huelva), Spain. The plants described are from high elevation nursery in Segovia, Spain, 3°59'W., 41°22'N., 2742 feet elevation. Plants were planted on June 12 in the first year and June 10 in the second year with a sample size of 2 repetitions every year and 120 plants per repetition per year.

GENERAL

TABLE 1

Table 1 shows the accumulated production of 1st Quality Fruit (g/plant) of the new variety 'Plapink 14103' when compared to varieties 'Adelita' and 'Lupita' ( U.S. Plant Pat. No. 25,171).

| Variety | End of September through end of December | Beginning in April through beginning of June | Total |
|---|---|---|---|
| 'Plapink 14103' | 1753.60 | 1931.70 | 3685.30 |
| 'ADELITA' | 1681.10 | 1086.70 | 2767.80 |
| 'LUPITA' | 1027.90 | 1636.60 | 2664.50 |

TABLE 2

Table 2 shows the Accumulated Total Yield of 1st and 2nd quality fruit (g/plant) of the new variety 'Plapink 14103' when compared to varieties 'Adelita' and 'Lupita'. Accumulated total yield: 1$^{st}$ and 2$^{nd}$ quality fruit (grames/plant)

| Variety | 1st + 2nd Quality End of September through end of December | 1st + 2nd Quality Beginning in April through beginning of June | Total |
|---|---|---|---|
| 'Plapink 14103' | 1860.50 | 2030.10 | 3890.60 |
| 'ADELITA' | 1942.80 | 1369.20 | 3312.00 |
| 'LUPITA' | 1121.40 | 1662.60 | 2784.00 |

TABLE 3

Table 3 shows the production from the end of September through the end of December of First Quality Fruit (1st quality) and Second Quality Fruit (2nd quality) in g/plant, of the new variety 'Plapink 14103' when compared to varieties 'Adelita' and 'Lupita'.

| Variety | 1st Quality | 2nd Quality | TOTAL (1st Quality + 2nd Quality) | % 2nd Quality |
|---|---|---|---|---|
| 'Plapink 14103' | 1753.60 | 106.90 | 1860.50 | 5.74 |
| 'ADELITA' | 1681.10 | 261.70 | 1942.80 | 13.47 |
| 'LUPITA' | 1027.40 | 93.50 | 1121.40 | 8.33 |

% 2nd Quality = (2nd Quality/TOTAL) × 100

TABLE 4

Table 4 shows production from the beginning of April through the beginning of June of First Quality Fruit (1st quality) and Second Quality Fruit (2nd quality) in g/plant, of the new variety Plapink 14103' when compared to the varieties 'Adelita' and 'Lupita'.

| Variety | 1st Quality | 2nd Quality | TOTAL (1st Quality + 2nd Quality) | % 2nd Quality |
|---|---|---|---|---|
| 'Plapink 14103' | 1931.70 | 98.40 | 2030.10 | 4.84 |
| 'ADELITA' | 1086.70 | 282.50 | 1369.20 | 20.60 |
| 'LUPITA' | 1636.60 | 26.00 | 1662.60 | 1.56 |

% 2nd Quality = (2nd Quality/TOTAL) × 100

TABLE 5

Table 5 shows the weight (g/Fruit) in two production periods: September to December, and April to June of the new variety 'Plapink 14103' when compared to the varieties 'Adelita' and 'Lupita'.

| Variety | End September to end of December | Beginning April to beginning June |
|---|---|---|
| 'Plapink 14103' | 5.6-5.0 | 5.5-4.8 |
| 'ADELITA' | 5.5 4.8 | 5.0-4.1 |
| 'LUPITA' | 5.4-4.7 | 4.9-4.1 |

WEIGHT is shown as the average weight per fruit (g/fruit) in First Quality Fruits.

TABLE 6

Table 6 shows a comparison of an analysis of the fruit from the new variety 'Plapink 14103' and the varieties 'Adelita' and 'Lupita'.
FRUIT ANALYSIS

| | 'Adelita' | 'Plapink 14103' | 'Lupita' |
|---|---|---|---|
| Humidity & Volatile Matter (%) | 86.2 | 87.4 | 89.2 |
| Dry Matter (%) | 13.8 | 12.6 | 10.8 |
| pH (to 20°) | 3.00 | 3.00 | 3.1 |
| Acidity as Anhydride Citric (%) | 2.4 | 16 | 2.2 |
| Soluble Solids (°Brix) | 10.9 | 9.7 | 9.00 |
| Maturity Index | 4.5 | 6.1 | 4.1 |
| Content in Ascorbic Acid (ppm) | 261 | 274 | 259 |
| Dominant Tonality (nm) | 515 | 515 | 515 |
| Luminosity: Transmittance to 460 nm | 22.65 | 37.14 | 23.3 |

The following definitions apply:

Dry Matter refers to the residual weight left from the trituration of the fruit after the drying process at a temperature of 103° C.±2° C. until reaching constant weight. (%) Dry Matter=(Weight Dry Matter/Weight Fresh Matter)×100

Humidity & Volatile Matter represents the content in volatile matters and water of the fruits. (%) Humidity & Volatile Matter=100−% Dry Matter Maturity Index refers to the relation between Soluble solids and Acidity as Anhydride Citric.

Maturity Index=Soluble solids/Acidity as Anhydride Citric

DETAILED DESCRIPTION OF THE NEW VARIETY

The following additional information is provided to further describe the new variety. Data is from plants growing in containers of 48 liters of capacity and they are described during cultivar's primocane.

PLANT

*Habit.*—Arching.
*Vigor.*—Medium.

Cultivar's primocane cane:
*Length.*—Approximately 200 cm to 280 cm.
*Diameter.*—Approximately 0.8 cm to 1.2 cm.
*Texture.*—Smooth.
*Internode length.*—Approximately 5.9 cm to 7.1 cm.
*Cross section.*—Rounded.
*Pubescence.*—Absent.
*Anthocyanin coloration of apex during rapid grow period.*—Absent.
*Anthocyanin coloration of current season's cane.*—Absent or very weak.
*Cane color.*—About RHS green group near 141 D to 141 C.

Spines:
*Shape.*—Conical.
*Density.*—Medium.
*Number/cm.*—Approximately 4 to 6.
*Length.*—Approximately 0.15 cm to 0.25 cm.
*Width.*—Approximately 0.20 cm to 0.30 cm at the base.
*Apex.*—Slightly curved.
*Color.*—RHS greyed-purple group color near 183 B to 183 A.
*Flexibility.*—Highly flexible.

LEAF

*Type.*—Compound.
*Number of leaflets.*—3.
*Arrangement of lateral leaflets.*—Touching.
*Overlapping of lateral leaflets with terminal leaflet.*—Present.
*Upperside color.*—About RHS green group color near 137 C to 137 B.
*Underside color.*—About RHS green group color near 138 C to 138 B.
*Length.*—Approximately 20.0 cm to 22.5 cm.
*Width.*—Approximately 20.0 cm to 21.5 cm.
*Profile of leaflets in cross section.*—Concave.
*Relief between veins.*—Weak.

Lateral leaflet:
*Shape.*—Elliptic.
*Length.*—Approximately 10.0 cm to 11.5 cm.
*Width.*—Approximately 6.5 cm to 7.0 cm.
*Shape of tip.*—Acuminate.
*Shape of base.*—Obtuse.
*Shape of margin.*—Double serrate.
*Upperside rugosity.*—Weak.
*Underside texture.*—Smooth.
*Upperside color.*—About RHS green group color (near 137 C to 137 B).
*Underside color.*—About RHS green group color (near 138 C to 138 B).
*Venation pattern.*—Reticulate or penniveined.
*Upperside venation coloration.*—About RHS yellow-green group color near 145 D to 145 C.
*Underside venation coloration.*—About RHS yellow-green group color near 144 D to 145 C.

Terminal leaflet:
*Length/width ratio.*—Longer than broad.
*Length.*—Approximately 12.5 cm to 13.5 cm.
*Width.*—Approximately 10.0 cm to 10.5 cm.
*Cross section.*—Concave.
*Upperside color.*—About RHS green group color near 137 C to 137 B.
*Underside color.*—About RHS green group color near 138 C to 138 B.
*Shape of leaflet.*—Ovate.
*Shape of tip.*—Acuminate.
*Shape of bas.*—Rounded.
*Shape of margin.*—Double serrate.
*Upperside rugosity.*—Weak.
*Underside texture.*—Smooth.
*Venation pattern.*—Reticulate or penniveined.
*Upperside venation coloration.*—About RHS yellow-green group color near 145 D to 145 C.
*Underside venation coloration.*—About RHS yellow-green group color near 144 D to 145 C.

Rachis:
*Length between the terminal leaflet and adjacent lateral leaflet.*—Approximately 3.0 cm to 3.5 cm.
*Coloration.*—About RHS yellow green group color near 144 D to 145 C.

Petiole:
*Color.*—About RHS yellow green group color near 145 D to 145 C.
*Petiolule length.*—Approximately 5.5 cm to 6.0 cm.
*Petiole length* (*rachis with petiolule*).—Approximately 8.5 cm to 9.5 cm.
*Diameter.*—Approximately 2.5 mm to 3.0 mm in the petiolule and approximately 2.0 mm to 2.5 mm in the rachis.
*Spines.*—Few.
*Petiole texture.*—Smooth.

Stipule:
*Quantity per leaf.*—2.
*Shape.*—Erect.
*Length.*—Approximately 9.0 mm to 10.0 mm.
*Width.*—Very narrow, approximately 0.3 mm to 0.4 mm.
*Color* (*both surfaces*).—About RHS yellow green group color near 145 D to 145 C.

Flower bud:
*Shape.*—Trapezoidal.
*Diameter.*—Approximately 1.1 cm to 1.5 cm.
*Length.*—Approximately 1.5 cm to 1.9 cm.
*Color.*—About RHS green group near 138 D to 138 C.

Pedicel:
*Length.*—Approximately 3.5 cm to 4.0 cm.
*Diameter.*—Approximately 2.0 mm to 2.5 mm.
*Pedicel color.*—About RHS green group near 143 D to 143 C.
*Surface texture.*—Smooth.
*Density of spines.*—Medium to many.

FLOWER

*Diameter.*—Approximately 1.0 cm to 1.5 cm.
*Number of pistils per flower.*—About 80 to 95.
*Pistil length.*—Approximately 3.5 mm to 4.0 mm.
*Ovary shape.*—Pyriform.
*Ovary length.*—Medium.
*Ovary width.*—Narrow.
*Ovary color.*—About RHS green group color near 142 D to 142 C.
*Style length.*—Approximately 0.10 cm to 0.15 cm.
*Style color.*—About RHS yellow-green group color (near 145 D).
*Number of stamens per flower.*—About 90 to 110.
*Stamen length.*—Approximately 0.3 cm to 0.4 cm.
*Stamen shape.*—Cylindrical lengthened.
*Stamen color.*—About RHS green-white group color near 157 D to 157 C.
*Pollen amount.*—Moderate.
*Pollen color.*—About RHS yellow green group color near 153 C to 153 B.

Petal:
*Number of petals per flower.*—About 5.
*Shape.*—Narrow elliptical.
*Length.*—Approximately 7.0 mm to 8.0 mm.
*Width.*—Approximately 3.0 mm to 4.0 mm.
*Apex shape.*—Flat rounded.
*Base shape.*—Narrow.
*Margin.*—Smooth and regular.
*Texture.*—Smooth.
*Color* (*both surfaces*).—About RHS white group color near 155 C.

Sepal:
*Number of sepals per flower.*—About 5.
*Shape.*—Triangular.
*Length.*—Approximately 9.0 mm to 10.5 mm.
*Width.*—Approximately 5.0 mm to 6.0 mm.
*Apex shape.*—Acuminate.
*Base shape.*—Large at the base forming the calyx.
*Margin.*—Smooth and regular.
*Texture.*—Smooth.
*Color.*—About RHS green group color near 145 C to 145 B.

Peduncles:
*Length.*—Approximately 16.5 cm to 18.0 cm.
*Diameter.*—Approximately 4.0 mm to 4.5 mm.
*Surface texture.*—Smooth.
*Density of spines.*—Sparse to medium.
*Color.*—About RHS green group near 143 D to 143 C.

FRUIT

*Shape.*—Broad conical.
*Length.*—Approximately 2.2 cm to 2.5 cm.
*Width.*—Approximately 2.1 cm to 2.4 cm.
*Color.*—About RHS red group color near 41 B to 41 A.
*Number of drupelets per fruit.*—Approximately 105 to 110.
*Size of single drupelet.*—Approximately 0.35 to 0.40 cm.
*Drupelet arrangement around the berry.*—Aligned.
*Glossiness.*—Strong.
*Firmness.*—Firm.
*Adherence to plug.*—Weak.
*Diameter hollow center.*—Approximately 1.0 cm to 1.2 cm.

Receptacle:
*Length.*—Approximately 1.1 cm to 1.3 cm.
*Diameter.*—Approximately 0.8 cm to 1.0 cm.
*Shape.*—Conical.
*Color.*—About RHS yellow-white group near 158 D to 158 C.

Seed:
*Number of seeds per drupelet.*—1.
*Shape.*—Slightly reniform.
*Color.*—About RHS greyed-orange group near 164 C to 164 B.
*Surface texture.*—Wrinkled.

Fruit bearing type: Both on previous year's cane in autumn and current year's cane in spring.

Fruiting lateral cane:
*Number of fruit per fruiting lateral cane.*—About 10 to 15 fruits.
*Average number of fruit per node.*—About 1 to 2 fruits.

GENERAL

*Date of planting.*—About June 10 in the farm of La Mogalla, in Cartaya (Huelva), Spain, about 7°W, 37°N, 45 feet elevation.
*Time of flowering data.*—10% flowering on primocane occurs about September 6 with first mature fruits about October 11 (15-20 g/plant), with a maximum production at the end of November.

STORAGE QUALITIES

'Plapink 14103' fruit maintains its quality characteristics for about 48 hours when kept under refrigeration at temperatures of about 2° C. Additionally, the fruit's color remains substantially the same. The shelf life of 'Plapink 14103' is good.

USE/MARKET

The berries of 'Plapink 14103' are suitable for consumption as fresh fruit. Also, they are suitable for processing.

DISEASE RESISTANCE

No particular sensitivity to any disease or pest has been observed for 'Plapink 14103'.

What is claimed is:

1. A new and distinct variety of raspberry plant named 'PLAPINK 14103' as herein described and illustrated.

* * * * *